(12) United States Patent
Jang et al.

(10) Patent No.: US 11,608,304 B2
(45) Date of Patent: Mar. 21, 2023

(54) METHOD FOR PREPARING CYCLODODECENE AND SYNTHESIS DEVICE THEREFOR

(71) Applicant: HANWHA SOLUTIONS CORPORATION, Seoul (KR)

(72) Inventors: Namjin Jang, Daejeon (KR); Kyuho Song, Daejeon (KR); Youngjin Kim, Daejeon (KR); Wook Jeong, Daejeon (KR)

(73) Assignee: Hanwha Chemical Corporation, Seoul (KR)

( * ) Notice: Subject to any disclaimer, the term of this patent is extended or adjusted under 35 U.S.C. 154(b) by 256 days.

(21) Appl. No.: 16/958,181

(22) PCT Filed: Oct. 23, 2018

(86) PCT No.: PCT/KR2018/012534
§ 371 (c)(1),
(2) Date: Jun. 26, 2020

(87) PCT Pub. No.: WO2019/132210
PCT Pub. Date: Jul. 4, 2019

(65) Prior Publication Data
US 2021/0070673 A1    Mar. 11, 2021

(30) Foreign Application Priority Data
Dec. 28, 2017    (KR) .................. 10-2017-0182978

(51) Int. Cl.
*C07C 5/05*    (2006.01)
*B01J 8/06*    (2006.01)
(Continued)

(52) U.S. Cl.
CPC .................. *C07C 5/05* (2013.01); *B01J 8/06* (2013.01); *B01J 19/0066* (2013.01); *B01J 27/13* (2013.01); *B01J 31/02* (2013.01); *C07C 13/273* (2013.01)

(58) Field of Classification Search
CPC ......... C07C 5/05; C07C 13/275; C07C 45/28; C07C 2601/20; C07C 49/413; C07C 13/273; C07C 2521/04; C07C 2523/44; C07C 2523/46; C07C 2531/24; B01J 19/0006; B01J 19/0066; B01J 19/1856;
(Continued)

(56) References Cited

U.S. PATENT DOCUMENTS 5,177,278 A    1/1993    Sanchez
5,180,870 A    1/1993    Paciello
(Continued)

FOREIGN PATENT DOCUMENTS

DE    19856862 A1    6/2000
JP    H5331076 A    12/1993
(Continued)

*Primary Examiner* — Sharon Pregler
(74) *Attorney, Agent, or Firm* — The Webb Law Firm

(57) ABSTRACT

A method for preparing cyclododecene and a synthesis device therefor, of the present invention, remarkably increase the conversion ratio of cyclododecatriene and selectivity of cyclododecene, can minimize the costs required for equipment and processing, are practical, reduce processing time, and are industrially advantageous to mass production in comparison with a conventional method and device.

15 Claims, 4 Drawing Sheets

(51) Int. Cl.
*B01J 19/00* (2006.01)
*B01J 27/13* (2006.01)
*B01J 31/02* (2006.01)
*C07C 13/273* (2006.01)

(58) Field of Classification Search
CPC ............ B01J 19/2415; B01J 2219/0004; B01J 2219/00051; B01J 2219/00162; B01J 2231/645; B01J 27/13; B01J 31/02; B01J 31/0207; B01J 31/0267; B01J 31/04; B01J 4/002; B01J 4/004; B01J 8/06
See application file for complete search history.

(56) References Cited

U.S. PATENT DOCUMENTS

| | | | |
|---|---|---|---|
| 6,080,372 A | 6/2000 | Machado | |
| 7,253,329 B2 | 8/2007 | Herwig et al. | |
| 7,838,705 B2 * | 11/2010 | Teles | C07C 45/28 568/363 |
| 2005/0065387 A1 | 3/2005 | Beller et al. | |

FOREIGN PATENT DOCUMENTS

| | | | |
|---|---|---|---|
| JP | 3861567 B2 | 12/2006 |
| JP | 4436839 B2 | 3/2010 |
| JP | 4523301 B2 | 8/2010 |

* cited by examiner

METHOD FOR PREPARING CYCLODODECENE AND SYNTHESIS DEVICE THEREFOR

CROSS-REFERENCE TO RELATED APPLICATIONS

This application is the United States national phase of International Application No. PCT/KR2018/012534 filed Oct. 23, 2018, and claims priority to Korean Patent Application No. 10-2017-0182978 filed Dec. 28, 2017, the disclosures of which are hereby incorporated by reference in their entirety.

TECHNICAL FIELD

The present invention relates to a method and device for preparing cyclododecene.

BACKGROUND ART

Synthesis of cyclododecene (CDEN) by selective hydrogenation starting from cyclododecatriene (CDT) has frequently been described in the literature, and many studies have been conducted to increase a yield of cyclododecene.

In general, in the above reaction, hydrogenation of cyclododecatriene including trans-1,5,9-cyclododecatriene proceeds stepwise via diene, mainly trans,trans-1,5-cyclododecadiene, cis,trans-1,5-cyclododecadiene, and an isomer mixture of trans-cyclododecene and cis-cyclododecene that are almost in equilibrium, to obtain cyclododecan (CDAN).

In order to synthesize cyclododecene at a high conversion ratio, hydrogenation by using a homogeneous catalyst and an amine compound by a Ru complex of cyclododecatriene is disclosed in U.S. Pat. No. 5,180,870 A. However, it is difficult to separate the catalyst and the amine compound from the cyclododecatriene, and cyclododecene, which is a product, may be contaminated with amine.

In preparation of cyclododecene by using a metal oxide catalyst, hydrogenation by gas/liquid/solid mass transfer in a liquid phase, continuous three-step hydrogenation and continuous gas phase hydrogenation in a fixed bed, and the like may be carried out by a heterogeneous catalyst.

As described above, extensive studies on a method for synthesizing cyclododecene have been conducted in order to increase the yield of cyclododecene; however, practical methods for industrially utilizing this and devices for the same are insufficient.

Specifically, in order to industrially utilize cyclododecene, cyclododecene is required to be synthesized in large quantities, and process efficiency such as equipment or maintenance of a device for this is required to be high. As an example, since a batch reactor is not suitable for industrial mass production of cyclododecene, a continuous flow stirred reactor is generally used in order to increase a scale of a reaction process and to allow a continuous reaction to proceed. However, in a case where a continuous flow process is used using the continuous flow stirred reactor, a yield and a selectivity of a product may be reduced, and it is difficult to achieve the optimal conversion ratio and selectivity under laboratory conditions. As an alternative, a tubular reactor may be applied. However, when an inner diameter of the tubular reactor is too large, a back mixing problem may occur, and when a length of the tubular reactor is increased, it is difficult to configure the equipment, and process operation efficiency such as maintenance may be excessively reduced.

A method for synthesizing cyclododecene capable of being implemented in an industrial scale and performed by using selective heterogeneous hydrogenation starting from cyclododecatriene using a readily available catalyst is disclosed in Japanese Patent Publication No. JP 4523301 B2. However, in the above patent, since a general fixed bed reactor is used in order to implement the industrial scale, the selectivity of cyclododecene is about 62 to 90%, which is significantly low.

Therefore, it is required to conduct studies on a method for preparing cyclododecene and a device for synthesizing cyclododecene that are capable of implementing both a conversion ratio of cyclododecatriene and a selectivity of cyclododecene at a high level and easily implementing industrial mass production of cyclododecene by synthesis.

DISCLOSURE

Technical Problem

An embodiment of the present invention is directed to providing a method for preparing cyclododecene and a device for synthesizing cyclododecene that are capable of implementing a conversion ratio of cyclododecatriene and a selectivity of cyclododecene at a significantly high level.

In addition, another embodiment of the present invention is directed to providing a method for preparing cyclododecene and a device for synthesizing cyclododecene that are capable of minimizing a cost required for equipment and processes, being practical, reducing process time, and being advantageous in industrial mass production of cyclododecene as compared with the related art, while implementing the above embodiment.

Technical Solution

In one general aspect, a method for synthesizing cyclododecene (CDEN) according to the present invention includes a hydrogenation step of partially hydrogenating cyclododecatriene (CDT) to synthesize cyclododecene, wherein cyclododecatriene and hydrogen ($H_2$) sequentially pass through a continuous stirred-tank reactor and a tubular reactor (plug flow reactor) and react with each other in the continuous stirred-tank reactor and the tubular reactor to synthesize cyclododecene.

In the method for synthesizing cyclododecene according to an exemplary embodiment of the present invention, the following Expression 1 may be satisfied. In the following Expression 1, $\tau_{1C}$ is a residence time of a reactant or a product in the continuous stirred-tank reactor, and $\tau_{1P}$ is a residence time of a reactant or a product in the tubular reactor.

$$1 \leq \tau_{1P}/\tau_{1C} \leq 9 \quad \text{[Expression 1]}$$

In an exemplary embodiment of the present invention, the continuous stirred-tank reactor may be obtained by sequentially connecting a first continuous stirred-tank reactor and a second continuous stirred-tank reactor.

In the method for synthesizing cyclododecene according to an exemplary embodiment of the present invention, the following Expression 2 may be satisfied. In the following Expression 2, $\tau_{1C}$ and $\tau_{2C}$ are a residence time of a reactant or a product in the first continuous stirred-tank reactor and a residence time of a reactant or a product in the second continuous stirred-tank reactor, respectively, and $\tau_{1P}$ is a residence time of a reactant or a product in the tubular reactor.

$$0.1 \leq \tau_{2C}/\tau_{1C} \leq 0.9$$

$$1 \leq \tau_{1P}/\tau_{1C} \leq 9 \quad \text{[Expression 2]}$$

In an exemplary embodiment, the cyclododecene may be synthesized by hydrogenation to the cyclododecatriene in a solvent containing ethanol, and may be synthesized by the reaction under a catalyst containing ruthenium chloride, triphenylphosphine (TPP), and formaldehyde.

In an exemplary embodiment of the present invention, a molar ratio of the ruthenium chloride to the triphenylphosphine may be 1:110 to 130.

In an exemplary embodiment of the present invention, a molar ratio of the triphenylphosphine to the formaldehyde may be 1:1.5 to 2.

In an exemplary embodiment of the present invention, in the hydrogenation step, a catalyst activator containing acetic acid may be further used.

In an exemplary embodiment of the present invention, the catalyst may be used in an amount of 1 to 7 parts by weight with respect to 100 parts by weight of the cyclododecatriene.

In an exemplary embodiment of the present invention, the reaction may be performed at a pressure of 10 to 80 bar and a temperature of 130 to 170° C.

In another general aspect, a device for synthesizing cyclododecene by partially hydrogenating cyclododecatriene according to the present invention includes: a continuous stirred-tank reactor into which cyclododecatriene and hydrogen are introduced to synthesize cyclododecene; and a tubular reactor into which the cyclododecene or a mixture including the cyclododecene is introduced from the continuous stirred-tank reactor to synthesize cyclododecene.

In still another general aspect, a device for synthesizing cyclododecene by partially hydrogenating cyclododecatriene according to the present invention includes: a first continuous stirred-tank reactor into which cyclododecatriene and hydrogen are introduced to synthesize cyclododecene; a second continuous stirred-tank reactor into which the cyclododecene or a mixture including the cyclododecene is introduced from the first continuous stirred-tank reactor to synthesize cyclododecene; and a tubular reactor into which the cyclododecene or a mixture including the cyclododecene is introduced from the second continuous stirred-tank reactor to synthesize cyclododecene.

In the device for synthesizing cyclododecene according to an exemplary embodiment of the present invention, the following Expression 3 may be satisfied. In following Expression 3, $V_{1C}$ is a volume of a reaction space of the continuous stirred-tank reactor, and $V_{1P}$ is a volume of a reaction space of the tubular reactor.

$$1 \leq V_{1P}/V_{1C} \leq 9 \quad \text{[Expression 3]}$$

In the device for synthesizing cyclododecene according to an exemplary embodiment of the present invention, the following Expression 4 may be satisfied. In following Expression 4, $V_{1C}$ and $V_{2C}$ are a volume of a reaction space of the first continuous stirred-tank reactor and a volume of a reaction space of the second continuous stirred-tank reactor, respectively, and $V_{1P}$ is a volume of a reaction space of the tubular reactor.

$$0.1 \leq V_{2C}/V_{1C} \leq 0.9$$

$$1 \leq V_{1P}/V_{1C} \leq 9 \quad \text{[Expression 4]}$$

In an exemplary embodiment of the present invention, first hydrogen may be introduced into and reacted in the first continuous stirred-tank reactor, such that the cyclododecene may be synthesized, second hydrogen may be introduced into and reacted in the second continuous stirred-tank reactor, such that the cyclododecene may be synthesized, and third hydrogen may be introduced into and reacted in the tubular reactor, such that the cyclododecene may be synthesized.

Advantageous Effects

A method for preparing cyclododecene and a device for synthesizing cyclododecene of the present invention are capable of implementing a conversion ratio of cyclododecatriene and a selectivity of cyclododecene at a significantly high level, minimizing a cost required for equipment and processes, being practical, reducing process time, and being advantageous in industrial mass production of cyclododecene as compared with the related art.

Effects described herein that are expected by technical characteristics of the present invention and potential effects may be construed as the effects that are described in the present invention even if such effects are not described in the present invention.

BEST MODE

Figure 1:
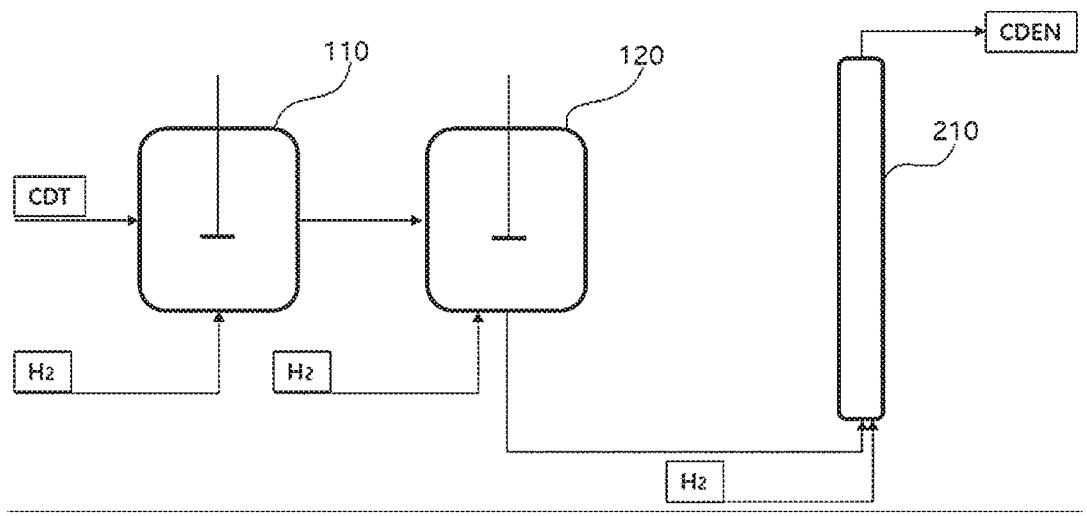
FIG. 1 is a view illustrating a composite reactor (first continuous stirred-tank reactor+second continuous stirred-tank reactor+tubular reactor) for synthesizing cyclododecene according to an exemplary embodiment of the present invention.

Hereinafter, a method for preparing cyclododecene and a device for synthesizing cyclododecene according to the present invention will be described in detail with reference to the accompanying drawings.

The drawings described in the present invention are provided by way of example so that the idea of the present invention can be sufficiently transferred to those skilled in the art. Therefore, the present invention is not limited to the drawings suggested, but may be modified in different forms. In addition, the drawings will be exaggerated in order to clarify the idea of the present invention.

Technical terms and scientific terms used in the present specification have the general meanings understood by those skilled in the art to which the present invention pertains unless otherwise defined, and a description for the known function and configuration obscuring the present invention will be omitted in the following description and the accompanying drawings.

Singular forms of the terms used in the present invention may be construed as including plural forms unless otherwise indicated.

Unless otherwise stated in the present invention, a unit of "%" used unclearly refers to "wt %".

Unlike a batch reactor, a method and device for synthesizing cyclododecene through a continuous flow in which a reactant is continuously injected and a product is continuously discharged is used in the present invention, which may minimize a cost required for equipment and processes, may be practical, and may be advantageous in industrial mass production of cyclododecene as compared with the related art. In addition, a reaction proceeds in a state where two continuous stirred-tank reactors and one or more tubular reactors are sequentially connected in series, such that the conversion ratio of cyclododecatriene, which is a reactant, and a selectivity of cyclododecene, which is a product, are significantly high.

That is, the method for synthesizing cyclododecene and the device for synthesizing cyclododecene according to the present invention may implement the conversion ratio of the reactant and the selectivity of the product at a significantly high level while adopting a continuous flow reaction advantageous in industrial mass production of cyclododecene. Therefore, energy efficiency of a preparation process may be improved, and a plant cost, an operating cost, and a plant maintenance cost are reduced, which may be very advantageous to be applied to an actual industry.

Hereinafter, the method for synthesizing cyclododecene according to the present invention will be described in detail.

The method for synthesizing cyclododecene (CDEN) according to the present invention is a method for synthesizing cyclododecene including a hydrogenation step of partially hydrogenating cyclododecatriene (CDT) to synthesize cyclododecene, in which cyclododecatriene and hydrogen ($H_2$) sequentially pass through a continuous stirred-tank reactor and a tubular reactor and react with each other in the continuous stirred-tank reactor and the tubular reactor. In this case, the continuous stirred-tank reactor and the tubular reactor may be independently one reactor, or two or more continuous stirred-tank reactors and tubular reactors may be connected in series or in parallel.

The continuous stirred-tank reactor may refer to a continuous stirred-tank reactor (CSTR), a gas-induced stirred tank reactor (GIST), or those connected in series or in parallel. Specifically, examples of the continuous stirred-tank reactor may include a single CSTR, a single GIST, two or more CSTRs connected in series or in parallel, two or more GISTs connected in series or in parallel, and one or more CSTRs and one or more GISTs connected in series or in parallel. These reactors may refer to known reactors generally used for synthesis of a reactant in the art.

The GIST is a continuous gas-induced stirred tank reactor, and may refer to a reactor that is the same as the CSTR but has an additional gas discharge structure for improving stirring efficiency at a stirrer of the CSTR, specifically, at a stirring rotor of the CSTR. In an exemplary embodiment of the present invention, it may be preferable that the GIST is used instead of the CSTR or one or more GISTs are used, because the conversion ratio and the selectivity may be further increased and a residence time may be significantly reduced to increase the process efficiency.

The tubular reactor may refer to a plug flow reactor (PFR), a bubble column reactor (BCR), or those connected in series or in parallel. Specifically, examples of the tubular reactor may include a single PFR, a single BCR, two or more PFRs connected in series or in parallel, two or more BCRs connected in series or in parallel, and one or more PFRs and one or more BCRs connected in series or in parallel. The bubble column reactor has a tubular shape that allows the reactant and the product to be subjected to a continuous process. These reactors may refer to known reactors generally used for synthesis of a reactant in the art.

In the present invention, reactants containing cyclododecatriene and hydrogen sequentially pass through the continuous stirred-tank reactor and the tubular reactor and react with each other in the continuous stirred-tank reactor and the tubular reactor, such that the conversion ratio of the reactant and the selectivity of the product may be significantly increased. The order of arranging the respective reactors is one of the important factors for implementing the above effects. For example, when the tubular reactor is arranged in the front of the continuous stirred-tank reactor, a high conversion ratio of a reactant and a high selectivity of a product may not be implemented in the final reaction product. In addition, when the reactor is constituted by only continuous stirred-tank reactors, the conversion ratio and the selectivity are not excellent, and when the reactor is constituted by only tubular reactors, commercialization is limited due to difficulty of industrial mass production of a product.

In the present invention, a residence time ($\tau$) of each of cyclododecatriene and hydrogen, which are reactants, in the reactor, affects the conversion ratio of the reactant and the selectivity of the product. Thus, the reactor is preferably designed and operated so as to satisfy the following Expression 1. However, the present invention is not limited thereto.

$$1 \leq \tau_{1P}/\tau_{1C} \leq 9 \qquad \text{[Expression 1]}$$

In Expression 1, $\tau_{1C}$ is a residence time of a reactant or a product in the continuous stirred-tank reactor, and $\tau_{1P}$ is a residence time of a reactant or a product in the tubular reactor.

As described in Expression 1, it may be preferable that a ratio of the residence times in the reactors is satisfied, because both the conversion ratio of the reactant and the selectivity of the product may be implemented at a significantly high level.

In an exemplary embodiment of the present invention, as the continuous stirred-tank reactor, one continuous stirred-tank reactor may be used or two or more continuous stirred-tank reactors connected in series or in parallel may be used. Two or more continuous stirred-tank reactors connected in series may be preferably used. In a case where the continuous stirred-tank reactor is obtained by sequentially connecting a first continuous stirred-tank reactor and a second continuous stirred-tank reactor, for example, in a case where the continuous stirred-tank reactor obtained by sequentially connecting a first continuous stirred-tank reactor, a second continuous stirred-tank reactor, and a tubular reactor is used (including a case of connecting two continuous stirred-tank reactors in series), the conversion ratio of cyclododecatriene and the selectivity of cyclododecene may be further increased.

In the method for synthesizing cyclododecene according to an exemplary embodiment of the present invention, the following Expression 2 may be satisfied.

$$0.1 \leq \tau_{2C}/\tau_{1C} \leq 0.9$$

$$1 \leq \tau_{1P}/\tau_{1C} \leq 9 \quad \text{[Expression 2]}$$

In Expression 2, $\tau_{1C}$ is a residence time of a reactant or a product in the first continuous stirred-tank reactor, $\tau_{2C}$ is a residence time of a reactant or a product in the second continuous stirred-tank reactor, and $\tau_{1P}$ is a residence time of a reactant or a product in the tubular reactor.

As described in Expression 2, it may be preferable that a ratio of the residence times in the reactors is satisfied, because both the conversion ratio of the reactant and the selectivity of the product may be implemented at a further significantly high level.

The hydrogenation step is a step of partially hydrogenating cyclododecatriene to synthesize cyclododecene.

In an exemplary embodiment of the present invention, the cyclododecene may be synthesized by hydrogenation to the cyclododecatriene in a solvent containing ethanol, and may be synthesized by the reaction under a catalyst containing ruthenium chloride, triphenylphosphine (TPP), and formaldehyde.

The reaction between the reactants may be further activated in the partial hydrogenation due to the ethanol having a high dielectric constant, which may increase the conversion ratio and the selectivity. The amount of ethanol used is not limited as long as hydrogenation to cyclododecatriene may be carried out. Preferably, the ethanol may be injected to the reactor at a flow rate at which a content of the ethanol is 1 to 10 parts by weight with respect to 100 parts by weight of the cyclododecatriene. However, this is only a preferred example, and the present invention is not limited thereto.

The triphenylphosphine forms a complex in the ruthenium chloride and serves as a catalyst for the partial hydrogenation. The reaction may be further activated under the presence of formaldehyde.

In a preferred example, the ruthenium chloride and the triphenylphosphine may be injected to the reactor at a flow rate at which a molar ratio of the ruthenium chloride to the triphenylphosphine is 1:110 to 130. When the reactants react with each other through reactors in which one or more continuous stirred-tank reactors and one or more tubular reactors are sequentially connected in series, in a case where ruthenium chloride and triphenylphosphine are used so that the above molar ratio is satisfied, more preferably, in a case where the above molar ratio is satisfied while satisfying the residence time described above, the conversion ratio and the selectivity may be significantly increased. However, this is only a preferred example, and the present invention is not limited thereto.

In a preferred example, the triphenylphosphine and the formaldehyde may be injected to the reactor at a flow rate at which a molar ratio of the triphenylphosphine to the formaldehyde is 1:1.5 to 2. When the reactants react with each other through reactors in which one or more continuous stirred-tank reactors and one or more tubular reactors are sequentially connected in series, in a case where triphenylphosphine and formaldehyde are used so that the above molar ratio is satisfied, more preferably, in a case where the above molar ratio is satisfied while satisfying the residence time described above, the conversion ratio and the selectivity may be further increased. However, this is only a preferred example, and the present invention is not limited thereto.

In an exemplary embodiment of the present invention, in the hydrogenation step, a catalyst activator containing acetic acid may be further used. When the acetic acid is injected to the reactor, a reaction of a ruthenium chloride-triphenylphosphine complex catalyst is further activated, and thus, the conversion ratio and the selectivity may be further increased. As a preferred example, the acetic acid may be injected to the reactor at a flow rate at which a content of the acetic acid is 0.01 to 2 parts by weight to 100 parts by weight of the cyclododecatriene. However, this is only a preferred example, and the present invention is not limited thereto.

In an exemplary embodiment of the present invention, the amount of the catalyst used is not limited as long as the reactants may sufficiently react with each other. Preferably, the catalyst may be injected or charged to the reactor at a flow rate at which a content of the catalyst is 1 to 7 parts by weight with respect to 100 parts by weight of the cyclododecatriene. However, this is only a preferred example in order to increase the conversion ratio and the selectivity, and the present invention is not limited thereto.

In an exemplary embodiment of the present invention, the reaction may be performed at a pressure of 10 to 80 bar, and preferably 20 to 40 bar. However, this is only a preferred example in order to increase the conversion ratio and the selectivity, and the present invention is not limited thereto.

In an exemplary embodiment of the present invention, the reaction may be performed at a temperature of 120 to 180° C., preferably 130 to 175° C., and more preferably 140 to 170° C. However, this is only a preferred example in order to increase the conversion ratio and the selectivity, and the present invention is not limited thereto.

The cyclododecene prepared according to the present invention may be used as an intermediate for synthesizing laurolactam. In a case where the cyclododecene prepared by using the method or device for synthesizing cyclododecene according to the present invention is used as an intermediate for synthesizing laurolactam, since a selectivity of a target product is very high, a conversion ratio and a selectivity are significantly excellent in the final step for synthesizing laurolactam, even though an obtained product that may include an unreacted reactant, an intermediate product, a by-product, and the like that are obtained from the synthesis method or the synthesis device according to the present invention may be used as the intermediate as it is.

A method for synthesizing laurolactam by using the method or device for synthesizing cyclododecene according to the present invention may include: a) a step of synthesizing cyclododecanone by an oxidation reaction of the cyclododecene with nitrous oxide; b) a step of synthesizing cyclododecanoneoxime by an oximation reaction of the cyclododecanone; and c) a step of synthesizing laurolactam by a Beckmann rearrangement reaction of the cyclododecanoneoxime.

Hereinafter, the device for synthesizing cyclododecene according to the present invention will be described in detail.

The device for synthesizing cyclododecene according to the present invention is a device for synthesizing cyclododecene by partially hydrogenating cyclododecatriene. The device for synthesizing cyclododecene may include a continuous stirred-tank reactor into which cyclododecatriene and hydrogen are introduced to synthesize cyclododecene; and a tubular reactor into which the cyclododecene or a mixture including the cyclododecene is introduced from the continuous stirred-tank reactor to synthesize cyclododecene. In this case, the mixture may include hydrogen.

As described above, the continuous stirred-tank reactor and the tubular reactor may be independently one reactor, or two or more continuous stirred-tank reactors and tubular reactors may be connected in series or in parallel.

The device for synthesizing cyclododecene according to an exemplary embodiment of the present invention is a device for synthesizing cyclododecene by partially hydrogenating cyclododecatriene. The device for synthesizing cyclododecene may include a first continuous stirred-tank reactor into which cyclododecatriene and hydrogen are introduced to synthesize cyclododecene; a second continuous stirred-tank reactor into which the cyclododecene or a first mixture including the cyclododecene is introduced from the first continuous stirred-tank reactor to synthesize cyclododecene; and a tubular reactor into which the cyclododecene or a second mixture including the cyclododecene is introduced from the second continuous stirred-tank reactor to synthesize cyclododecene. In this case, the first mixture and the second mixture may independently include hydrogen.

As described above, in the method for synthesizing cyclododecene, the ratio of the residence times in the reactors is one of the important factors that may significantly increase the conversion ratio of the reactant and the selectivity of the product. In the present invention, in a case where a composite reactor in which the following Expression 3 or 4 is satisfied is used, it is possible to provide a device for synthesizing cyclododecene in which a ratio of the residence times may be automatically controlled without special adjustment of a flow ratio between materials to be introduced into the reactors.

In the device for synthesizing cyclododecene according to the present invention in which the ratio of the residence times in the reactors described above, that is, Expression 1 or 2 is satisfied, the following Expression 3 or 4 may be satisfied. However, the present invention is not limited thereto.

$$1 \leq V_{1P}/V_{1C} \leq 9 \quad \text{[Expression 3]}$$

$$0.1 \leq V_{2C}/V_{1C} \leq 0.9$$

$$1 \leq V_{1P}/V_{1C} \leq 9 \quad \text{[Expression 4]}$$

In Expression 3, $V_{1C}$ is a volume of a reaction space of the continuous stirred-tank reactor, and $V_{1P}$ is a volume of a reaction space of the tubular reactor.

In Expression 4, $V_{1C}$ and $V_{2C}$ are a volume of a reaction space of the first continuous stirred-tank reactor and a volume of a reaction space of the second continuous stirred-tank reactor, respectively, and $V_{1P}$ is a volume of a reaction space of the tubular reactor.

When a ratio of the volumes of the reaction spaces in the reactors in which Expression 3 or 4 is satisfied, Expression 1 or 2 automatically is satisfied without special adjustment of a flow ratio between materials to be introduced into the reactors, for example, even when reactants are injected at the same flow rate. Thus, the conversion ratio and the selectivity may be significantly increased, and the process efficiency may be excellent because a separate control for the flow rate of the material to be introduced is not necessarily required.

In an exemplary embodiment of the present invention, as illustrated in FIG. 1 as an example, first hydrogen may be introduced into and reacted in the first continuous stirred-tank reactor, such that the cyclododecene may be synthesized, second hydrogen may be introduced into and reacted in the second continuous stirred-tank reactor, such that the cyclododecene may be synthesized, and third hydrogen may be introduced into and reacted in the tubular reactor, such that the cyclododecene may be synthesized. By introducing each hydrogen into each reactor, unreacted cyclododecatriene is converted into cyclododecene, and thus, the conversion ratio may be significantly increased.

The term "reactor" used in the present invention may be adequately used depending on a scale of a process and environment, unless otherwise defined. Therefore, a specific element of the reactor that is not mentioned in the present invention is not limited. In addition, each reactor may include various inflow pipes into which a material is introduced or which are provided for introducing a material, outflow pipes, and connecting pipes that connect the inflow pipes to the outflow pipes, respectively. In addition, the use of specific devices for adjusting an inflow amount and an outflow amount is not limited because it is a matter that may be adequately adjusted by those skilled in the art.

In the synthesis method or the synthesis device according to the present invention, as the conversion ratio of cyclododecatriene and the selectivity of cyclododecene, the conversion ratio and the selectivity in the first continuous stirred-tank reactor may be 35 to 50% and 90 to 99%, respectively, the conversion ratio and the selectivity in the second continuous stirred-tank reactor may be 50 to 98% and 97 to 99.9%, respectively, and the conversion ratio and the selectivity in the tubular reactor may be 95 to 99% and 97 to 99.9%, respectively. That is, in the present invention, three different types of reactors are combined, and preferably, various components described above are further combined, such that the conversion ratio of cyclododecatriene may be significantly increased while minimizing the reduction of the selectivity of cyclododecene.

Hereinafter, the present invention will be described in detail with reference to examples. However, the examples are intended to describe the present invention in more detail, and the scope of the present invention is not limited by the following examples.

Example 1

Cyclododecene was synthesized using a composite reactor (first continuous stirred-tank reactor+second continuous stirred-tank reactor+tubular reactor) that satisfies the conditions of Table 1 and illustrated in FIG. 1 under the conditions of Table 1. In this case, the continuous stirred-tank reactor is denoted by CSTR, and the tubular reactor is denoted by BCR.

Specifically, to the first continuous stirred-tank reactor satisfying the following conditions of Table 1, ruthenium chloride ($RuCl_3$), triphenylphosphine (TPP), and formaldehyde were injected at a molar ratio of 1:110:220, acetic acid and ethanol were injected thereto, and then stirring was continuously performed at 800 rpm under conditions of 80° C. and 2 bar. After the respective components were sufficiently mixed with each other, cyclododecatriene and hydrogen gas ($H_2$) were continuously injected to the first continuous stirred-tank reactor under the following conditions of Table 1. The acetic acid and the ethanol were injected in amounts of 0.25 parts by weight and 5.27 parts by weight with respect to 100 parts by weight of the cyclododecatriene, respectively.

The mixture injected to and present in the first continuous stirred-tank reactor was transferred to the second continuous stirred-tank reactor, and hydrogen was additionally supplied to the second continuous stirred-tank reactor. The mixture discharged from the second continuous stirred-tank reactor was introduced into a lower portion of the tubular reactor, and hydrogen was additionally supplied to the tubular reactor. In this case, the hydrogen was evenly distributed and supplied by a gas nozzle and a dispersion plate. The mixture inside the tubular reactor was discharged by adjusting a pressure at a rear end of the tubular reactor.

TABLE 1

|  | First continuous stirred-tank reactor | Second continuous stirred-tank reactor | Tubular reactor |
|---|---|---|---|
| τ (time) | 0.4 | 0.2 | 2 |
| V (m³) | 1 | 0.5 | 5 |
| $V_{2C}/V_{1C}$ |  | 0.5 |  |
| $V_{1P}/V_{1C}$ |  | 5 |  |
| T (° C.) |  | 160 |  |
| P (bar) |  | 20 |  |

τ: Residence time
V: Internal volume of reactor
$V_{1C}$: Internal volume of first continuous stirred-tank reactor
$V_{2C}$: Internal volume of second continuous stirred-tank reactor
$V_{1P}$: Internal volume of tubular reactor
T: Internal temperature of reactor
P: Internal pressure of reactor Example 2

Each cyclododecene was synthesized in the same manner as that of Example 1, except that the reactors were independently operated 8 times so that the ratio of the residence times (τ) in the reactors of Table 2 was satisfied instead of the residence time of Table 1. In this case, the ratio of the residence times (τ) was controlled by adjusting the flow rate of each reactant.

TABLE 2

| $\tau_{2C}/\tau_{1C}$ | $\tau_{1P}/\tau_{1C}$ |
|---|---|
| 0.1 | 5 |
| 0.2 | 5 |
| 0.8 | 5 |
| 1.0 | 5 |
| 0.5 | 1 |
| 0.5 | 2 |
| 0.5 | 8 |
| 0.5 | 10 |

Example 3

Each cyclododecene was synthesized by independently performing the operations 5 times in the same manner as that of Example 1, except that the molar ratio of ruthenium chloride to triphenylphosphine was changed to 1:80, 1:90, 1:100, 1:130, and 1:150.

Example 4

Each cyclododecene was synthesized by independently performing the operations 3 times in the same manner as that of Example 1, except that the molar ratio of triphenylphosphine to formaldehyde was changed to 1:1.0, 1:1.5, and 1:2.5.

Example 5

Each cyclododecene was synthesized by independently performing the operations 4 times in the same manner as that of Example 1, except that the reaction was performed at 10, 40, 50, and 80 bar instead of being performed at 20 bar.

Example 6

Cyclododecene was synthesized in the same manner as that of Example 1, except that the reaction was performed at 140° C. instead of being performed at 160° C.

Example 7

Cyclododecene was synthesized in the same manner as that of Example 1, except that a continuous gas-induced stirred tank reactor (GIST) was used instead of the CSTR.

Comparative Example 1

Cyclododecene was synthesized in the same manner as that of Example 1, except that one continuous stirred-tank reactor was used instead of the composite reactor of FIG. 1. In this case, the operation was performed under the following conditions of Table 3.

TABLE 3

|  | Comparative Example 1 One continuous stirred-tank reactor |
|---|---|
| τ (time) | 6 |
| V (m³) | 15 |
| T (° C.) | 160 |
| P (bar) | 20 |

τ: Residence time
V: Internal volume of reactor
T: Internal temperature of reactor
P: Internal pressure of reactor Comparative Example 2

Cyclododecene was synthesized in the same manner as that of Example 1, except that the reactor obtained by sequentially connecting the tubular reactor, the first continuous stirred-tank reactor, and the second continuous stirred-tank reactor was used instead of the composite reactor of FIG. 1, that is, except that the tubular reactor was arranged at the foremost portion of the composite reactor of FIG. 1.

Evaluation of Conversion Ratio and Selectivity According to Reactor Combination

In Example 1, the conversion ratio of cyclododecatriene and the selectivity of cyclododecene in each reactor were measured. The results are shown in Table 4.

TABLE 4

|  | First continuous stirred-tank reactor | Second continuous stirred-tank reactor | Tubular reactor |
|---|---|---|---|
| Conversion ratio (%) | 40.00 | 60.00 | 99.00 |
| Selectivity (%) | 99.33 | 99.20 | 98.00 |

In Comparative Example 1, the conversion ratio of PG-4T cyclododecatriene and the selectivity of cyclododecene were measured. The results are shown in Table 5.

TABLE 5

|  | Comparative Example 1 One continuous stirred-tank reactor | Comparative Example 2 Tubular reactor → First continuous stirred-tank reactor → Second continuous stirred-tank reactor |
|---|---|---|
| Conversion ratio (%) | 92 | 92 |
| Selectivity (%) | 92 | 93 |

As shown in Table 4, in Example 1 in which two continuous stirred-tank reactors and one tubular reactor were used, both the final conversion ratio and the final selectivity were 98% or higher, which were high. However, as shown in Table 5, in Comparative Example 1 in which the tubular reactor was not used, both the final conversion ratio and the final selectivity were 92% or lower, which were significantly low.

In Comparative Example 2, the conversion ratio of cyclododecatriene and the selectivity of cyclododecene in each reactor were measured. As a result, the final conversion ratio was 92% and the final selectivity was 93%, which were significantly low. Accordingly, it could be appreciated from Example 1 and Comparative Example 2 that differences between the final conversion ratios and the final selectivities were remarkable depending on the order of the reactors, even though two continuous stirred-tank reactors and one tubular reactor were used.

<Evaluation of Conversion Ratio and Selectivity According to Residence Time>

In Examples 1 and 2, the final conversion ratio of cyclododecatriene and the final selectivity according to the ratio of the residence times in the reactors were measured.

As a result, when $\tau_{2C}/\tau_{1C}$ satisfied 0.1 to 0.9 and $\tau_{1P}/\tau_{1C}$ satisfied 1 to 9, the conversion ratio and the selectivity were significantly higher than when $\tau_{2C}/\tau_{1C}$ and $\tau_{1P}/\tau_{1C}$ did not satisfy the above ranges.

<Evaluation of Conversion Ratio and Selectivity According to Molar Ratio of Ruthenium Chloride to Triphenylphosphine>

In Examples 1 and 3, the conversion ratios of cyclododecatriene and the selectivities of cyclododecene according to molar ratios of ruthenium chloride ($RuCl_3$) to triphenylphosphine (TPP) were measured. The results are shown in Table 7 and are illustrated in FIG. 2.

TABLE 7

| $RuCl_3$/TPP (mol ratio) | Conversion ratio (%) | Selectivity (%) |
|---|---|---|
| 1:80 | 80.0 | 99.2 |
| 1:90 | 86.6 | 99.1 |
| 1:100 | 92.6 | 99.0 |
| 1:110 | 99.9 | 98.0 |
| 1:130 | 98.4 | 98.4 |
| 1:150 | 96.5 | 99.1 |

Figure 2:
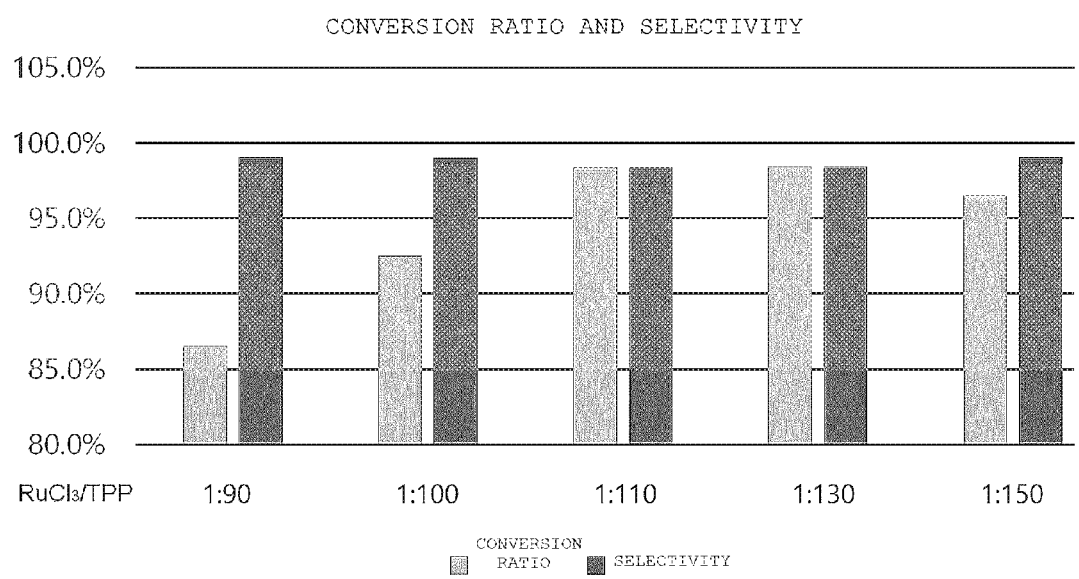
FIG. 2 illustrates results of measuring conversion ratios of cyclododecatriene and selectivities of cyclododecene according to molar ratios of ruthenium chloride ($RuCl_3$) to triphenylphosphine (TPP) in Examples 1 and 3.

As shown in Table 7 and illustrated in FIG. 2, it was confirmed that in a case where the molar ratio of ruthenium chloride to triphenylphosphine satisfied 1:110 to 1:130, both the conversion ratio and the selectivity were 98.4% or higher, which were very high levels, as compared to a case where the molar ratio of ruthenium chloride to triphenylphosphine was less than 1:110.

Therefore, it could be appreciated that the molar ratio of ruthenium chloride to triphenylphosphine is preferably 1:110 to 130 in order to satisfy both the conversion ratio and the selectivity at a high level of 98% or higher.

<Evaluation of Conversion Ratio and Selectivity According to Molar Ratio of Triphenylphosphine to Formaldehyde>

In Examples 1 and 4, the conversion ratios of cyclododecatriene and the selectivities of cyclododecene according to molar ratios of triphenylphosphine (TPP) to formaldehyde ($CH_2O$) were measured. The results are shown in Table 8 and are illustrated in FIG. 3.

TABLE 8

| $RuCl_3$/TPP (mol ratio) | TPP/$CH_2O$ (mol ratio) | Conversion ratio (%) | Selectivity (%) |
|---|---|---|---|
| 1:90 | 1:1.5 | 75 | 99.0 |
| 1:90 | 1:2.0 | 87 | 99.1 |
| 1:110 | 1:1.0 | 95.9 | 98.8 |
| 1:110 | 1:1.5 | 97.1 | 98.5 |
| 1:110 | 1:2.0 | 99.0 | 98.0 |
| 1:110 | 1:2.5 | 91.3 | 99.2 |

Figure 3:
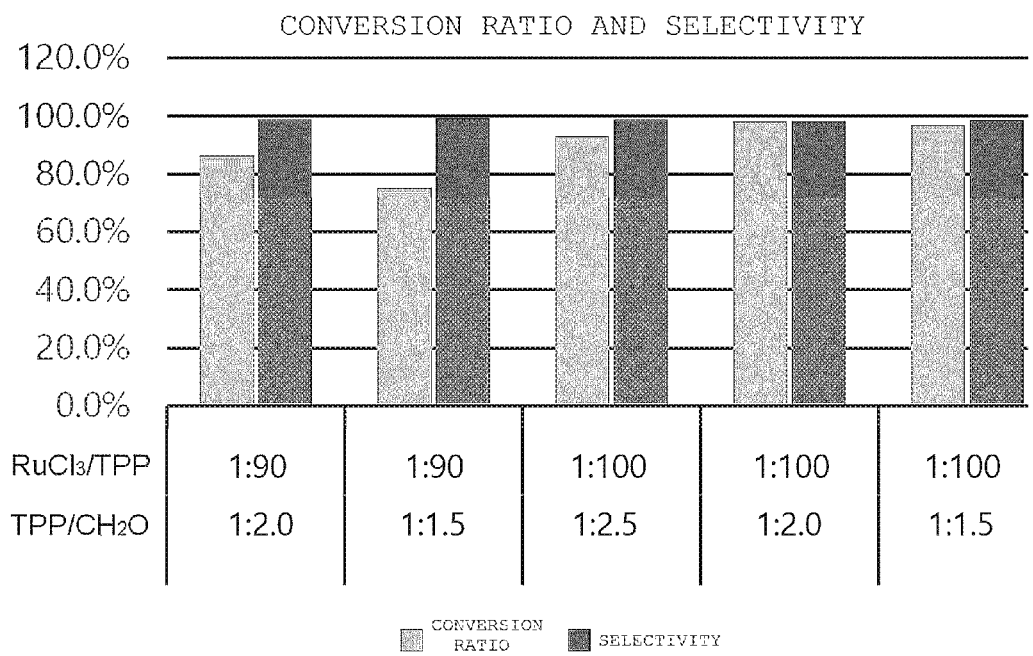
FIG. 3 illustrates results of measuring conversion ratios of cyclododecatriene and selectivities of cyclododecene according to molar ratios of triphenylphosphine (TPP) to formaldehyde ($CH_2O$) in Examples 1 and 4.

First, as shown in Table 8 and illustrated in FIG. 3, in a case where the molar ratio of ruthenium chloride to triphenylphosphine satisfied 1:110 to 130, the conversion ratio was significantly higher than in a case where the molar ratio did not satisfy the above range.

In addition, it was confirmed that in a case where the molar ratio of triphenylphosphine to formaldehyde satisfied 1:1.5 to 1:2.0, both the conversion ratio and the selectivity were 97.1% or higher, which were very high levels, as compared to a case where the molar ratio of triphenylphosphine to formaldehyde was less than 1:1.5.

Therefore, it could be appreciated that the molar ratio of triphenylphosphine to formaldehyde is preferably 1:1.5 to 2.0 in order to satisfy both the conversion ratio and the selectivity at a high level of 97% or higher.

<Evaluation of Conversion Ratio, Selectivity, and Reaction Time According to Reaction Pressure>

In Examples 1 and 5, conversion ratios of cyclododecatriene (CDT) and cyclododecadiene (CDDN), selectivities of cyclododecene (CDEN), and reaction times were measured according to the reaction pressures. The results were shown in Table 9 and illustrated in FIGS. 4 and 5.

TABLE 9

| Reaction pressure (bar) | Conversion ratio (%) | Selectivity (%) |
|---|---|---|
| 10 | 95.50 | 99.20 |
| 20 | 99.00 | 98.00 |
| 40 | 98.71 | 97.50 |
| 50 | 99.37 | 94.90 |
| 80 | 99.48 | 91.30 |

Figure 4:
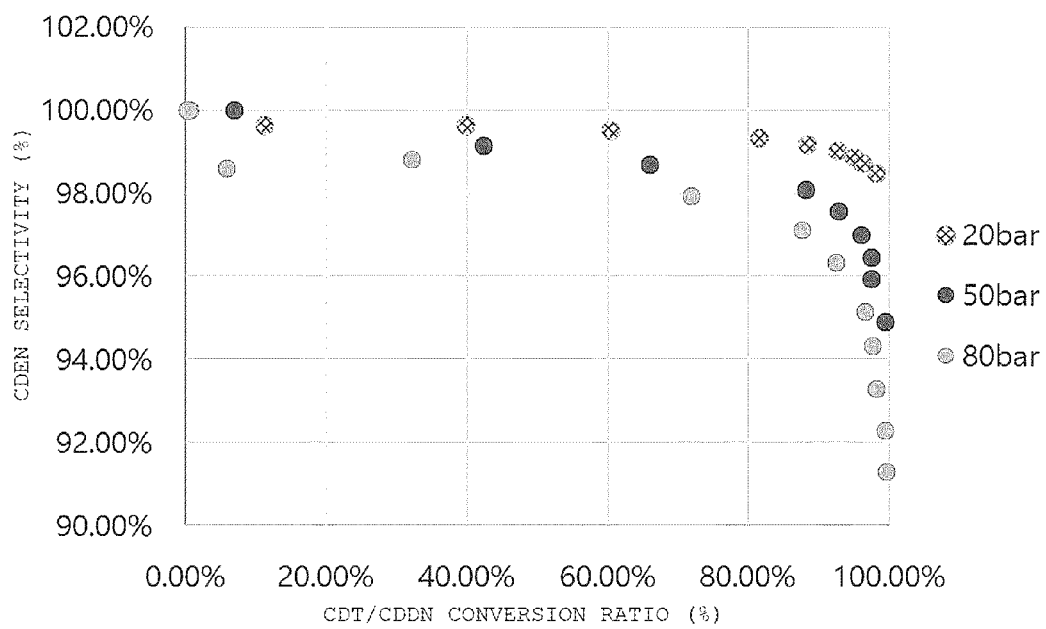
FIG. 4 illustrates results of measuring conversion ratios of cyclododecatriene (CDT) and cyclododecadiene (CDDN) and selectivities of cyclododecene (CDEN) according to reaction pressures in Examples 1 and 5.

As shown in Table 9 and illustrated in FIG. 4, it could be confirmed that in a case where the reaction pressure was 20 to 40 bar, both the conversion ratio and the selectivity were excellent at a very high level, as compared to a case where the reaction pressure was less than 20 bar, and in this case, the reaction time was significantly reduced until the conversion ratio reached, which was more suitable for the industrial use. In addition, in the case where the reaction pressure was 20 to 40 bar, the selectivity was excellent at a very high level, as compared to a case where the reaction pressure of more than 40 bar.

Accordingly, it could be appreciated that the reaction pressure is more preferably 20 to 40 bar, in order to satisfy both the conversion ratio and the selectivity at a high level and to increase the process efficiency such as the reduction in the reaction time.

Figure 5:
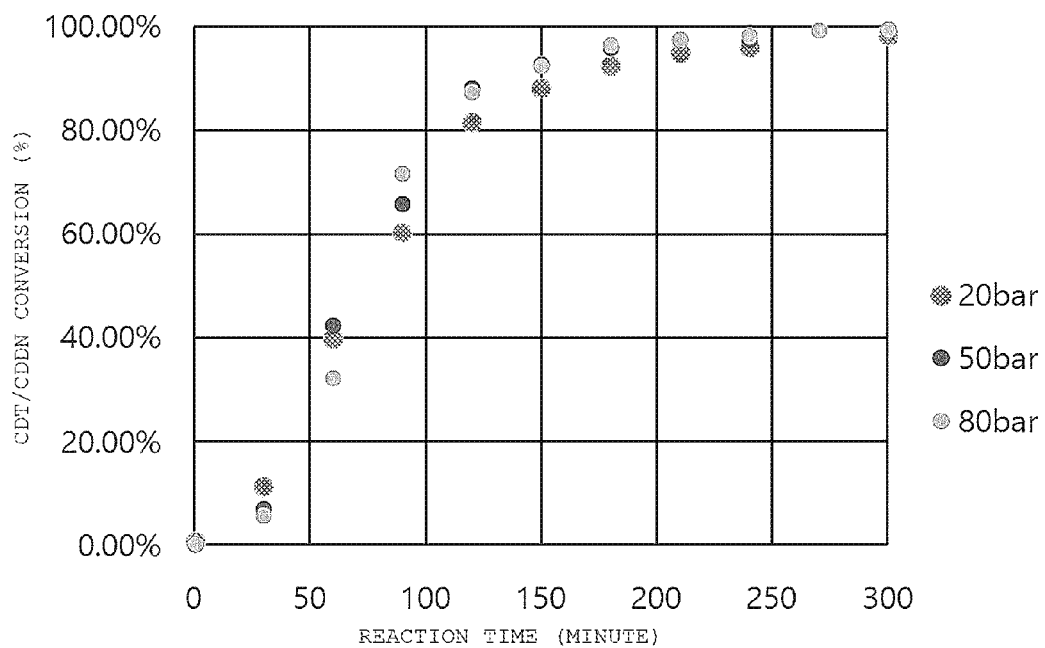
FIG. 5 illustrates results of measuring reaction times of cyclododecene (CDEN) synthesized according to the reaction pressures in Examples 1 and 5.

In addition, as illustrated in FIG. 5, it could be appreciated that, as the pressure is increased, a reaction rate is increased, and the selectivity is reduced.

<Evaluation of Mass Fraction According to Reaction Time>

Figure 6:
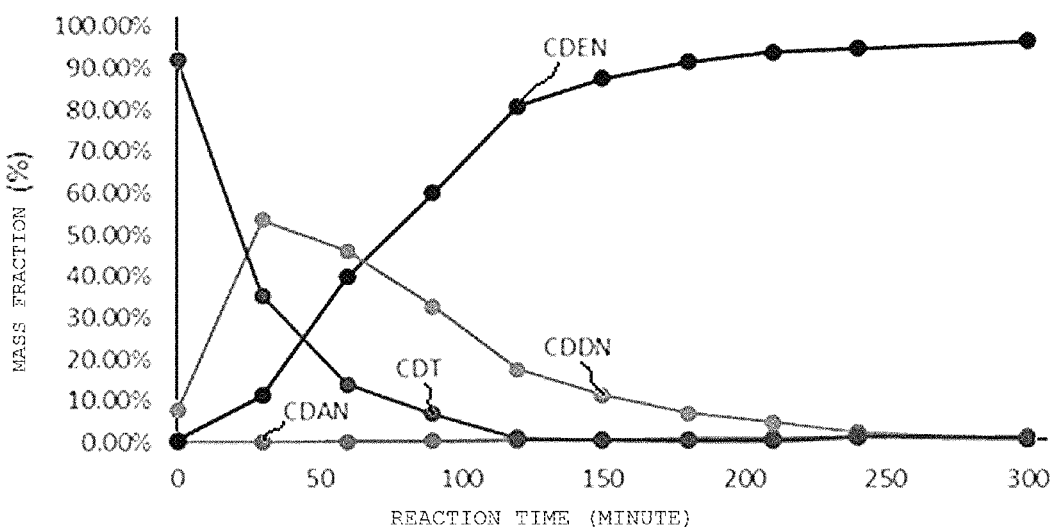
FIG. 6 illustrates results of measuring mass fractions according to reaction times (residence times) in Example 1.

In Example 1, the mass fraction according to the reaction time (reaction residence time) was measured by performing sampling during the reaction. The results are illustrated in FIG. 6. In FIG. 6, CDAN is cyclododecan, CDEN is cyclododecene, CDDN is cyclododecadiene, and CDT is cyclododecatriene.

<Evaluation of Conversion Ratio and Selectivity According to Types of Reactors (CSTR and GIST)>

Figure 7:
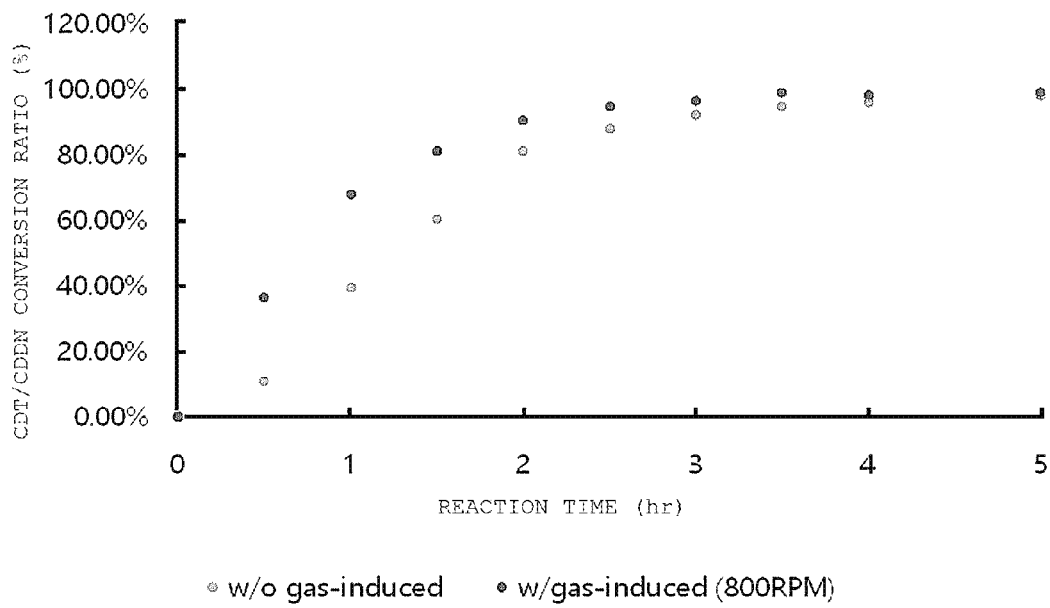
FIG. 7 illustrates results of measuring conversion ratios of cyclododecatriene (CDT) and cyclododecadiene (CDDN) according to the types of the reactors in Example 7.
Figure 8:
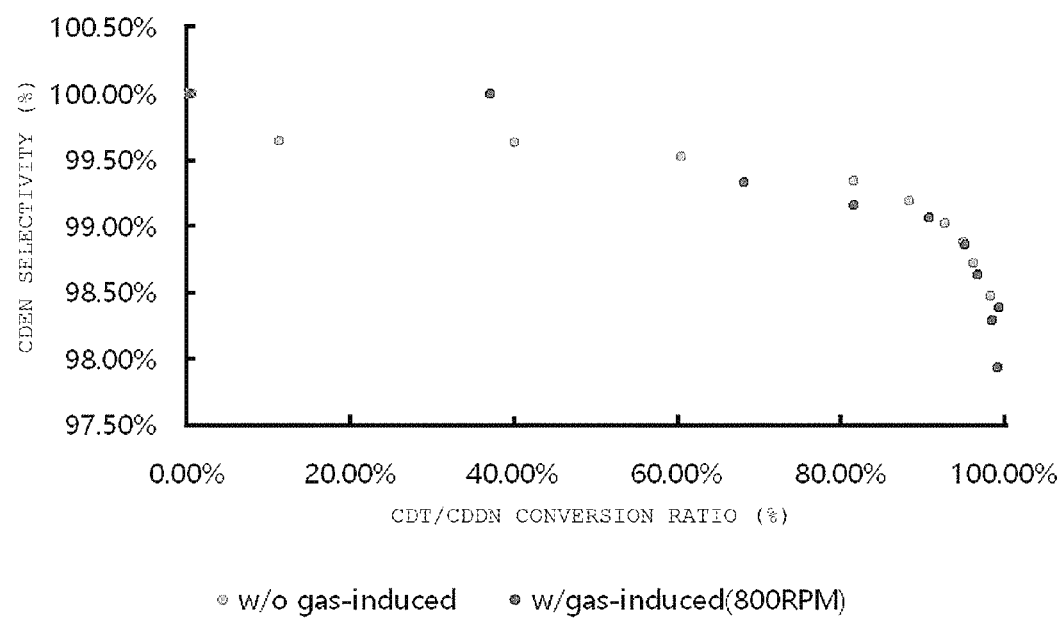
FIG. 8 illustrates results of measuring selectivities of cyclododecene (CDEN) according to the types of the reactors in Example 7.

Under the same reaction conditions as those in Example 1, in Example 7 in which both the first continuous stirred-tank reactor and the second continuous stirred-tank reactor were replaced with GISTs, the conversion ratios of cyclododecatriene (CDT) and cyclododecadiene (CDDN) and the selectivity of cyclododecene (CDEN) according to the types of the reactors were measured. The results are illustrated in FIG. 7.

As a result, it was confirmed that in Example 7, the conversion ratio was 99.14% and the selectivity was 98.38%, which were excellent in the conversion ratio and the selectivity while having half the residence time of Example 1, and in particular, the residence time was significantly reduced and the process efficiency was greatly improved.

DETAILED DESCRIPTION OF MAIN ELEMENTS

110: First continuous stirred-tank reactor
120: Second continuous stirred-tank reactor
210: Tubular reactor

The invention claimed is:

1. A method for synthesizing cyclododecene, comprising a hydrogenation step of partially hydrogenating cyclododecatriene to synthesize cyclododecene,
wherein cyclododecatriene and hydrogen sequentially pass through a continuous stirred-tank reactor and a tubular reactor and react with each other in the continuous stirred-tank reactor and the tubular reactor to synthesize cyclododecene.

2. The method of claim 1, wherein the following Expression 1 is satisfied, $$1 \leq \tau_{1P}/\tau_{1C} \leq 9 \quad \text{[Expression 1]}$$

(in Expression 1, $\tau_{1C}$ is a residence time of a reactant or a product in the continuous stirred-tank reactor, and $\tau_{1P}$ is a residence time of a reactant or a product in the tubular reactor).

3. The method of claim 1, wherein the continuous stirred-tank reactor is obtained by sequentially connecting a first continuous stirred-tank reactor and a second continuous stirred-tank reactor.

4. The method of claim 3, wherein the following Expression 2 is satisfied, $$0.1 \leq \tau_{2C}/\tau_{1C} \leq 0.9$$

$$1 \leq \tau_{1P}/\tau_{1C} \leq 9 \quad \text{[Expression 2]}$$

(in Expression 2, $\tau_{1C}$ and $\tau_{2C}$ are a residence time of a reactant or a product in the first continuous stirred-tank reactor and a residence time of a reactant or a product in the second continuous stirred-tank reactor, respectively, and Tip is a residence time of a reactant or a product in the tubular reactor).

5. The method of claim 1, wherein the cyclododecene is synthesized by hydrogenation to the cyclododecatriene in a solvent containing ethanol, and is synthesized by the reaction under a catalyst containing ruthenium chloride, triphenylphosphine, and formaldehyde.

6. The method of claim 5, wherein a molar ratio of the ruthenium chloride to the triphenylphosphine is 1:110 to 130.

7. The method of claim 5, wherein a molar ratio of the triphenylphosphine to the formaldehyde is 1:1.5 to 2.

8. The method of claim 5, wherein in the hydrogenation step, a catalyst activator containing acetic acid is further used.

9. The method of claim 5, wherein the catalyst is used in an amount of 1 to 7 parts by weight with respect to 100 parts by weight of the cyclododecatriene.

10. The method of claim 1, wherein the reaction is performed at a pressure of 10 to 80 bar and a temperature of 130 to 170° C.

11. A device for synthesizing cyclododecene by partially hydrogenating cyclododecatriene, the device comprising:
a continuous stirred-tank reactor into which cyclododecatriene and hydrogen are introduced to synthesize cyclododecene; and
a tubular reactor into which the cyclododecene or a mixture including the cyclododecene is introduced from the continuous stirred-tank reactor to synthesize cyclododecene.

12. The device of claim 11, wherein the following Expression 3 is satisfied, $$1 \leq V_{1P}/V_{1C} \leq 9 \quad \text{[Expression 3]}$$

(in Expression 3, $V_{1C}$ is a volume of a reaction space of the continuous stirred-tank reactor, and $V_{1P}$ is a volume of a reaction space of the tubular reactor).

13. A device for synthesizing cyclododecene by partially hydrogenating cyclododecatriene, the device comprising:
a first continuous stirred-tank reactor into which cyclododecatriene and hydrogen are introduced to synthesize cyclododecene;
a second continuous stirred-tank reactor into which the cyclododecene or a mixture including the cyclododecene is introduced from the first continuous stirred-tank reactor to synthesize cyclododecene; and
a tubular reactor into which the cyclododecene or a mixture including the cyclododecene is introduced from the second continuous stirred-tank reactor to synthesize cyclododecene.

14. The device of claim 13, wherein the following Expression 4 is satisfied, $$0.1 \leq V_{2C}/V_{1C} \leq 0.9$$

$$1 \leq V_{1P}/V_{1C} \leq 9 \quad \text{[Expression 4]}$$

(in Expression 4, $V_{1C}$ and $V_{2C}$ are a volume of a reaction space of the first continuous stirred-tank reactor and a volume of a reaction space of the second continuous stirred-tank reactor, respectively, and $V_{1P}$ is a volume of a reaction space of the tubular reactor).

15. The device of claim 13, wherein first hydrogen is introduced into and reacted in the first continuous stirred-tank reactor, such that the cyclododecene is synthesized, second hydrogen is introduced into and reacted in the second continuous stirred-tank reactor, such that the cyclododecene is synthesized, and third hydrogen is introduced into and reacted in the tubular reactor, such that the cyclododecene is synthesized.

* * * * *